United States Patent
Li et al.

(10) Patent No.: US 9,146,186 B2
(45) Date of Patent: Sep. 29, 2015

(54) ASSAY DEVICE AND METHOD AND ELECTRONIC DEVICE USING SAME

(75) Inventors: Cheng-Zhi Li, Guangdong (CN); Jun Zhang, Guangdong (CN); Jun-Wei Zhang, Guangdong (CN); Tsung-Jen Chuang, New Taipei (TW); Shih-Fang Wong, New Taipei (TW)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 759 days.

(21) Appl. No.: 13/275,326

(22) Filed: Oct. 18, 2011

(65) Prior Publication Data

US 2012/0253734 A1   Oct. 4, 2012

(30) Foreign Application Priority Data

Mar. 31, 2011   (CN) .......................... 2011 1 0080446

(51) Int. Cl.
  *G06F 19/00*   (2011.01)
  *G06M 11/04*   (2006.01)
  *G01N 9/24*   (2006.01)
  *G01N 9/36*   (2006.01)
  *G01N 23/00*   (2006.01)

(52) U.S. Cl.
  CPC .. G01N 9/24 (2013.01); G01N 9/36 (2013.01); G01N 23/00 (2013.01)

(58) Field of Classification Search
  CPC ....................................................... G01N 9/24
  USPC ........................................................ 702/128
  See application file for complete search history.

(56) References Cited

U.S. PATENT DOCUMENTS

| | | | | |
|---|---|---|---|---|
| 5,062,127 A | * | 10/1991 | Sayama et al. | 378/45 |
| 5,745,369 A | * | 4/1998 | Ukon | 702/28 |
| 7,529,337 B2 | * | 5/2009 | Matoba et al. | 378/45 |
| 2006/0126786 A1 | * | 6/2006 | Lee et al. | 378/70 |
| 2009/0086905 A1 | * | 4/2009 | Boyden et al. | 378/46 |

FOREIGN PATENT DOCUMENTS

CN   101405597 A   4/2009

OTHER PUBLICATIONS

Cullity, Element of X-Ray Diffraction, 1956, Addison-Wesley Publishing Company, Inc., p. 10-14.*
B. D. Cullity, Elements of X-Ray Diffraction, Mar. 1956, Addison Wesley Publishing Company, pp. 10-12, 468.*
B.D. Cullity, Element of X-Ray Diffraction, Copyright 1956, Addison Wesley Publishing Company, Inc.*

* cited by examiner

*Primary Examiner* — Andrew Schechter
*Assistant Examiner* — Peter Ngo
(74) *Attorney, Agent, or Firm* — Novak Druce Connolly Bove + Quigg LLP

(57) ABSTRACT

An assay device capable of assaying purity of a substance in an object includes a memory, an emitter, a receiver, a processing unit, and a display device. The memory stores names and standard densities of a number of substances. The emitter emits rays at the object. The receiver receives the rays reflected by the object. The processing unit calculates density of the object according to intensity of the emitted rays and intensity of the reflected rays. The processing unit further calculates purity of a selected substance in the object according to the density of the object and standard density of the selected substance stored in the memory, and outputs the calculated purity to the display device.

16 Claims, 2 Drawing Sheets

ASSAY DEVICE AND METHOD AND ELECTRONIC DEVICE USING SAME

BACKGROUND

1. Technical Field

The present disclosure relates to assay devices, and more particularly to an electronic device capable of performing an assay of a substance, and an assay method thereof.

2. Description of Related Art

Purity of a substance is an important parameter for evaluating an object. For example, when shopping for precious metals and gems, it is important to know the purity of the precious metals and gems.

What is needed, therefore, is a user friendly device capable of assaying purity of a substance.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the various views, and all the views are schematic.

DETAILED DESCRIPTION

Reference will now be made to the drawings to describe specific exemplary embodiments of the present disclosure in detail.

Figure 1:
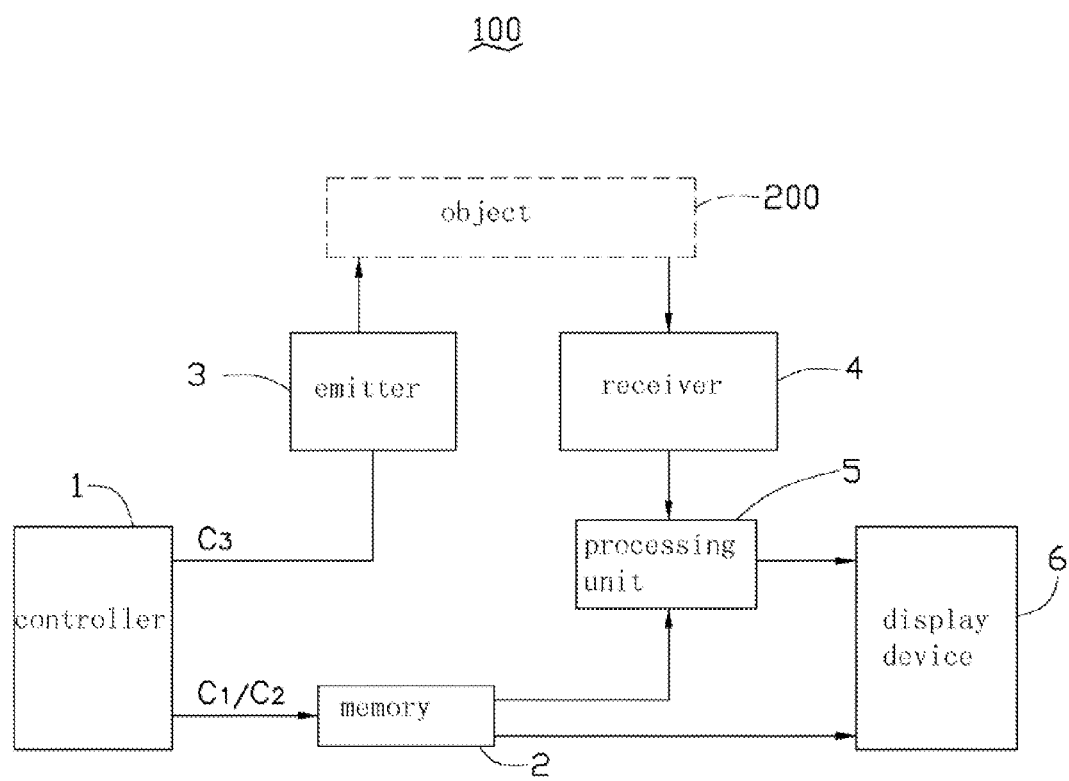
FIG. 1 is a block schematic diagram of an assay device including a controller, a memory, an emitter, a receiver, a processing unit, and a display device.

FIG. 1 is a block schematic diagram of an assay device 100 including a controller 1, a memory 2, an emitter 3, a receiver 4, a processing unit 5, and a display device 6. The assay device 100 may be incorporated in an electronic device (not shown) such as a mobile phone, or a PDA, for example. The controller 1 connects to the memory 2 and the emitter 3. The memory 2 further connects to the processing unit 5 and display device 6. The processing unit 5 further connects to the display device 6.

The memory 2 stores names and/or symbols and standard densities of a plurality of substances, such as, gold and silver, for example. In response to user-startup of the controller 1, the controller 1 provides control signals to the memory 2 and the emitter 3, according to user input of a name of a substance to be assayed. The user input may be via a keyboard or a touch panel which may be disposed on the assay device 100 or the electronic device incorporating the assay device 100, for example. The memory 2 outputs the names of the plurality of substances to the display device 6 in response to the user-startup of the controller 1, and further outputs a corresponding name and a corresponding standard density to the processing unit 5 in response to the input name.

The assay device 100 can be positioned near an object 200 within an emitting area of the emitter 3 and a receiving area of the receiver 4 directly pointed at the object 200. The emitter 3 emits β-rays to the object 200 based on the input name. The receiver 4 receives β-rays reflected back by the object 200, calculates the ratio of intensity of the received β-rays to intensity of the emitting β-rays to acquire reflectivity of the object 200, and outputs the calculated reflectivity to the processing unit 5. The intensity of the emitting β-rays may be pre-stored in the receiver 4, the emitter 3, or other memory component and retrieved at need. The processing unit 5 receives the calculated reflectivity from the receiver 4, and the standard density of the selected substance in the object 200 from the memory 2. The processing unit 5 further calculates density of the object 200 according to the calculated reflectivity, and calculates purity of the selected substance using the ratio of the calculated density of the object 200 to the standard density of the selected substance, in addition outputs the calculated purity of the selected substance to the display device 6. The display device 6 displays the names and the standard densities of the plurality of substances stored in the memory 2, and the calculated purity of the selected substance in the object 200.

Figure 2:
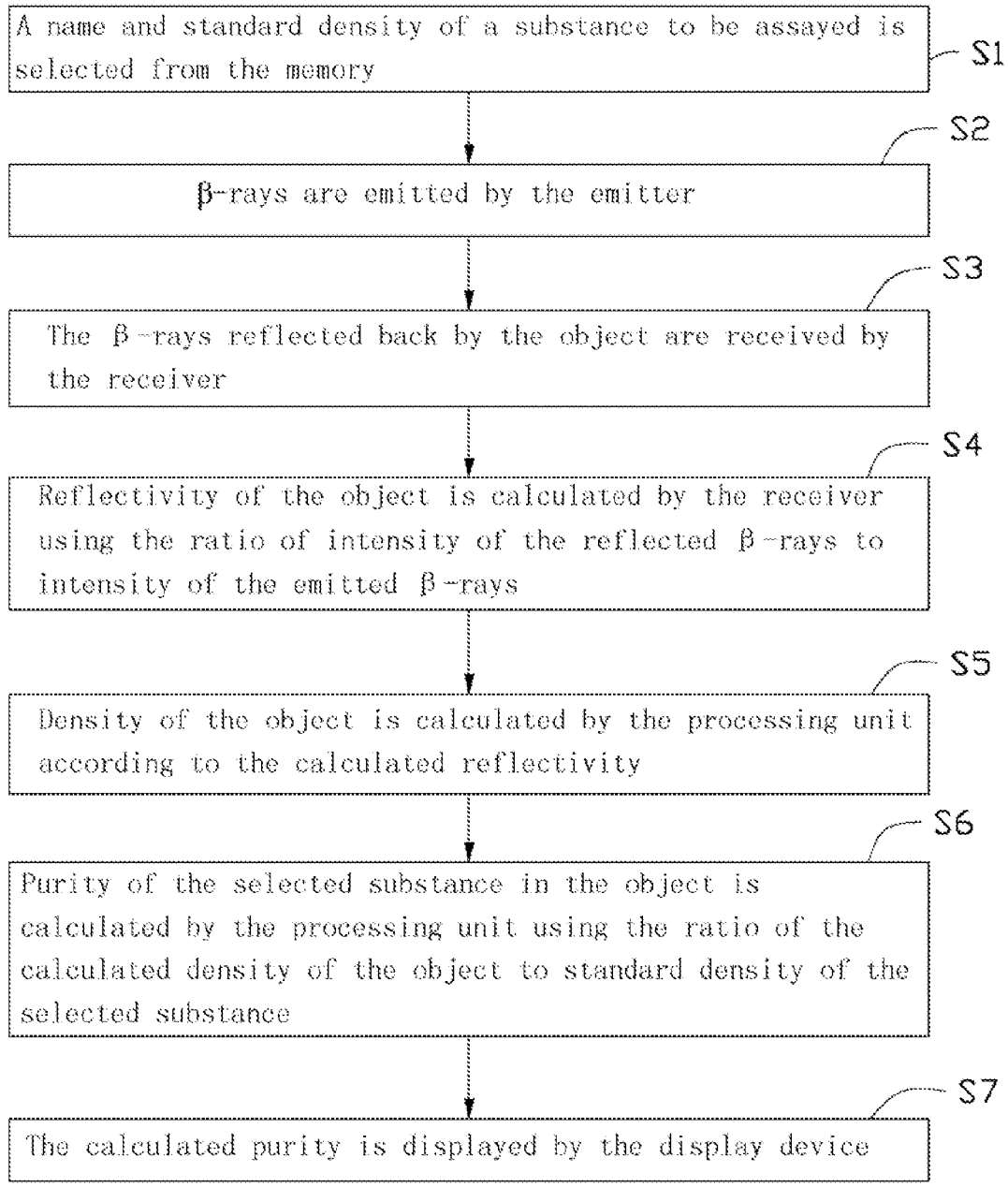
FIG. 2 is a flowchart of an exemplary assay method of the assay device for assaying purity of a substance shown in FIG. 1.

FIG. 2 is a flowchart of an exemplary assay method of the assay device 100 for assaying the purity of the substance shown in FIG. 1. It is understood that additional steps may be added, others deleted, and the order of the steps may change depending on the embodiment. In step S1 a name and standard density of a substance to be assayed is selected from the memory 2. In step S2, β-rays are emitted by the emitter 3. In step S3, the β-rays reflected back by the object 200 are received by the receiver 4. In step S4, reflectivity of the object 200 is calculated by the receiver 4 using the ratio of intensity of the reflected β-rays to intensity of the emitted β-rays. In step S5, density of the object 200 is calculated by the processing unit 5 according to the calculated reflectivity. In step S6, purity of the selected substance in the object 200 is calculated by the processing unit 5 using the ratio of the calculated density of the object 200 to standard density of the selected substance. In step S7, the calculated purity is displayed by the display device 6. A detailed description of the exemplary assay method of the assay device 100 for assaying the purity of the substance is further described as follows:

In step S1, the controller 1 correspondingly provides a first control signal $C_1$ to the memory 2 in response to the user-startup of the controller 1. The memory 2 outputs the names of the plurality of the substances to the display device 6 according to the first control signal $C_1$. The display device 6 displays the names of the plurality of the substances stored in the memory 2. The controller 1 further provides a second control signal $C_2$ to the memory 2 and provides a third control signal $C_3$ to the emitter 3 in response to the user input of the name of a to-be-assayed substance selected from the displayed substances. The memory 2 outputs the standard density of the selected substance to the processing unit 5 according to the second control signal $C_2$. The emitter 3 emits the β-rays to the object 200 according to the third control signal $C_3$.

As described, since the assay device 100 has the function for performing an assay of a substance, and the assay device 100 can be taken with the user anywhere and anytime for daily life, it is a friendly device for the user to assay the purity of the substance in precious metals or gems when they are shopping for the precious metals or the gems.

It should be pointed out that in alternative embodiments, the emitter 3 may also emit X-rays instead of the β-rays.

It is believed that the present embodiments and their advantages will be understood from the foregoing description, and it will be apparent that various changes may be made thereto without departing from the spirit and scope of the embodiments or sacrificing all of their material advantages.

What is claimed is:

1. An assay device, comprising:
   a controller outputting a first control signal in response to a user-startup of the controller, and a second control signal;

a display device;

a memory that stores names and standard densities of a plurality of substances, wherein the names of the plurality of substances are outputted to the display device according to the user-startup of the controller;

an emitter emitting rays at an object under control of the second control signal in response to a selected substance input by a user;

a receiver configured to receive the rays reflected back by the object; and a processing unit configured to calculate density of the object according to intensity of the emitted rays and intensity of the reflected rays, calculate purity of the selected substance in the object according to the calculated density of the object and standard density of the selected substance stored in the memory, and output the calculated purity to the display device; and wherein the assay device is incorporated in a mobile phone.

2. The assay device of claim 1, wherein the receiver further calculates reflectivity of the object using the ratio of the intensity of the reflected rays to the intensity of the emitted rays, and outputs the calculated reflectivity to the processing unit.

3. The assay device of claim 2, wherein the processing unit receives the calculated reflectivity, and calculates the density of the object based on the calculated reflectivity.

4. The assay device of claim 3, wherein the processing unit further calculates the purity of the selected substance using the ratio of the calculated density of the object to the standard density of the selected substance.

5. The assay device of claim 1, wherein the rays are rays selected from the group consisting of β-rays and X-rays.

6. A method for assaying purity of a substance, comprising:
providing an assay device incorporated in a mobile phone, the assay device comprising a memory that stores names and standard densities of a plurality of substances, and the names of the plurality of substances outputted according the user-startup of the controller, an emitter, a receiver, and a processing unit;

selecting a substance in an object to be assayed;

emitting rays at the object by the emitter under control of a first control signal in response to the selected substance input by a user;

receiving the reflected rays from the object by the receiver;

calculating density of the object according to intensity of the reflected rays and intensity of the emitted rays by the processing unit; and calculating purity of the selected substance in the object according to the calculated density of the object and standard density of the selected substance stored in the memory by the processing unit.

7. The method of claim 6, further comprising calculating reflectivity of the object according to the intensity of the reflected rays and the intensity of the emitted rays, and outputting the calculated reflectivity to the processing unit by the receiver.

8. The method of claim 7, wherein the processing unit calculates the density of the object according to the received reflectivity.

9. The method of claim 8, wherein the assay device further comprises a display device, the method further comprises the calculated purity is outputted to the display device.

10. The method of claim 9, wherein the assay device further comprises a controller, the method further comprises the names of the plurality of substances are outputted to the display device by the memory in response to startup of the controller.

11. The method of claim 10, further comprising a second control signal is outputted to the memory, and the standard density of the selected substance is outputted to the processing unit by the memory based on the first control signal.

12. A mobile phone comprising:
an assay device incorporated in the mobile phone, the assay device comprising:
a controller outputting a first control signal in response to a user-startup of the controller, and a second control signal;
a display device;
a memory that stores names and standard densities of a plurality of substances, wherein the names of the plurality of substances are outputted according to the user-startup of the controller;
an emitter emitting rays at an object under control of the second control signal in response to a selected substance input by a user;
a receiver configured to receive the rays reflected back by the object; and
a processing unit configured to calculate density of the object according to intensity of the emitted rays and intensity of the reflected rays, calculate purity of the selected substance in the object according to the calculated density of the object and standard density of the selected substance stored in the memory, and output the calculated purity to the display device.

13. The mobile phone of claim 12, wherein the receiver further calculates reflectivity of the object using the ratio of the intensity of the reflected rays to the intensity of the emitted rays, and outputs the calculated reflectivity to the processing unit.

14. The mobile phone of claim 13, wherein the processing unit receives the calculated reflectivity, calculates the density of the object based on the calculated reflectivity.

15. The mobile phone of claim 14, wherein the processing unit further calculates the purity of the selected substance using the ratio of the calculated density of the object to the standard density of the selected substance.

16. The mobile phone of claim 13, wherein the rays are rays selected from the group consisting of β-rays and X-rays.

* * * * *